(12) United States Patent
Winzinger et al.

(10) Patent No.: US 8,349,270 B2
(45) Date of Patent: Jan. 8, 2013

(54) APPARATUS FOR TREATING CONTAINERS INCLUDING CARRIER STERILISATION

(75) Inventors: Frank Winzinger, Regensburg (DE); Philipp Albers, Detmold (DE)

(73) Assignee: Krones AG (DE)

( * ) Notice: Subject to any disclaimer, the term of this patent is extended or adjusted under 35 U.S.C. 154(b) by 0 days.

(21) Appl. No.: 12/837,371

(22) Filed: Jul. 15, 2010

(65) Prior Publication Data

US 2011/0020172 A1    Jan. 27, 2011

(30) Foreign Application Priority Data

Jul. 18, 2009   (DE) .......................... 10 2009 033 809

(51) Int. Cl.
*A61L 2/00* (2006.01)
*B67D 1/08* (2006.01)
*B08B 3/04* (2006.01)
*A47L 15/00* (2006.01)

(52) U.S. Cl. ........ 422/292; 422/300; 422/302; 422/303; 422/304; 141/89; 141/234; 222/148; 134/104.1; 134/166 R; 15/59; 15/60

(58) Field of Classification Search .................... 422/28, 422/292, 300, 302–304; 141/89, 234; 222/148; 134/62, 65, 72–73, 104.1, 166 R, 17; 53/452, 53/167; 264/446; 15/21.1, 59, 60

See application file for complete search history.

(56) References Cited

U.S. PATENT DOCUMENTS

| | | | | |
|---|---|---|---|---|
| 5,740,844 | A | * | 4/1998 | Miller .............................. 141/90 |
| 6,158,596 | A | * | 12/2000 | Ohtsuka et al. ............ 211/41.18 |
| 2003/0015223 | A1 | * | 1/2003 | Jacksier et al. ............ 134/22.18 |
| 2005/0092390 | A1 | * | 5/2005 | Krulitsch ....................... 141/144 |
| 2010/0089009 | A1 | | 4/2010 | Till ................................ 53/452 |

FOREIGN PATENT DOCUMENTS

WO   WO 2008/125216   * 10/2008
WO   WO 2010/020530     2/2010

OTHER PUBLICATIONS

European Patent Office machine translation of the description section of WO 2008/125216.*

* cited by examiner

*Primary Examiner* — Jill Warden
*Assistant Examiner* — Monzer Chorbaji
(74) *Attorney, Agent, or Firm* — Hayes Soloway P.C.

(57) ABSTRACT

An apparatus for treating containers, including a transport device which transports the containers along a specified transport path, the transport device including a plurality of holding elements for holding the containers, with the holding elements being transported along the specified transport path. The apparatus includes a cleaning device for sterilizing the holding elements at least in sections.

20 Claims, 6 Drawing Sheets

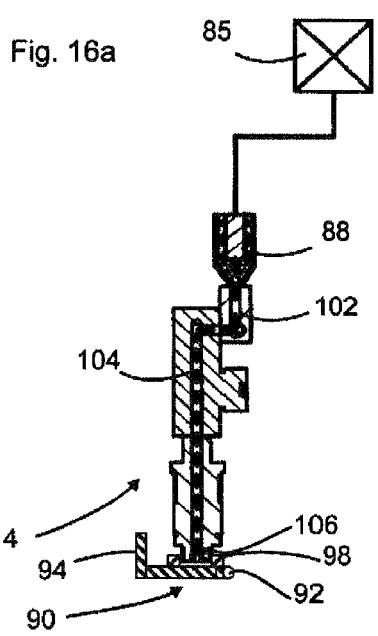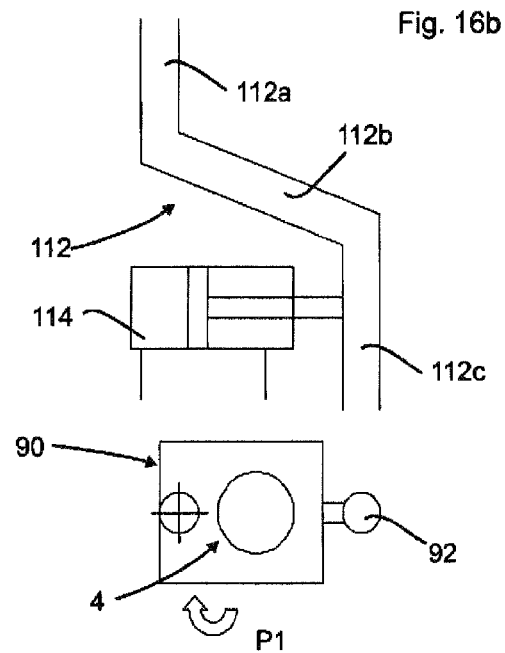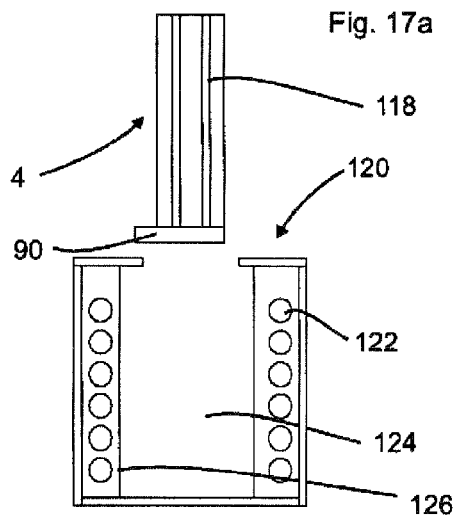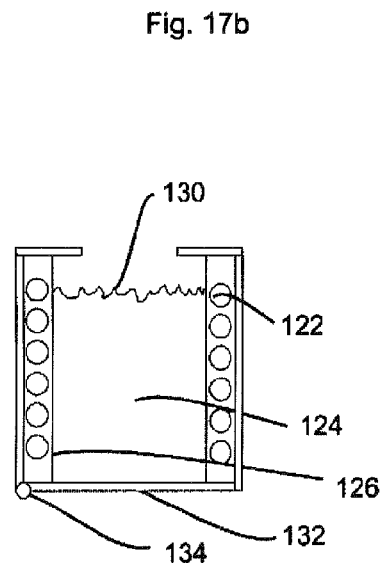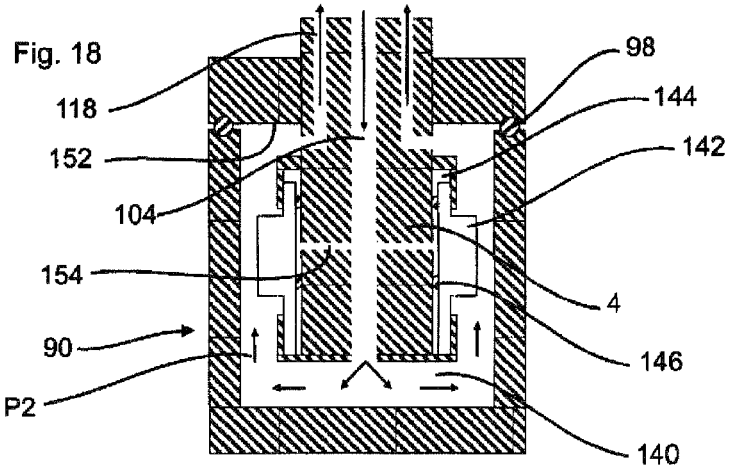

APPARATUS FOR TREATING CONTAINERS INCLUDING CARRIER STERILISATION

BACKGROUND OF THE INVENTION

The present invention relates to an apparatus and a method for treating containers. It has been known from the prior art for quite a long time that during the manufacture of plastic containers, for example of beverage bottles, plastic preforms are initially generated, which are subsequently heated and expanded into containers by blow moulding. The invention is in particular applicable to apparatus of this kind, however, it is to be noted that the apparatus according to the invention may also be used for other machinery such as for example machines for filling glass containers.

In the sector of the beverage producing industry it is important during the filling process to focus particularly on cleanliness and sterility. The various treatment steps of the containers require that the containers to be manufactured and filled are transported by a plurality of transport devices. This transport in turn can lead to contamination.

From WO 2008/125 216 A1, an apparatus for manufacturing containers and a method for manufacturing moulded bodies are known. In the context of this apparatus it is described that radiation means such as UV radiators are attached for example to a blowing wheel, and by means of these UV radiators, parts of the surfaces of the apparatus for manufacturing containers, such as for example housing walls, are cleaned. This apparatus thus allows a partially satisfactory sterilisation of machine parts to be carried out, however, especially the elements that carry the containers carry a particular risk factor with regard to contamination. This applies in particular to such holding elements which for transporting the preforms engage therein or for those that engage in the mouth of the containers.

The present invention is therefore based on the object of providing an apparatus and a method which allow an improved sterilisation effect and thus also an improved degree of purity of the system to be achieved.

SUMMARY OF THE INVENTION

An apparatus according to the invention for treating containers and in particular for moulding plastic preforms into plastic containers includes a transport device which transports the containers along a specified transport path, wherein the transport device includes a plurality of holding elements for holding the containers, which holding elements are moved along the specified transport path. According to the invention, the apparatus includes a cleaning device, in order to clean the holding elements at least in sections.

A cleaning device is understood to mean a device which is used for cleaning, in the broadest sense, another element or body. In particular, the cleaning device may be a sterilisation device which sterilises the body concerned or parts thereof. However, it would also be conceivable to provide for example a mechanically acting cleaning device which only cleans the body, but does not sterilise or degerm it. Apart from the term cleaning device, also the term sterilisation device will be used below. Thus, the cleaning device is preferably also used for sterilising the holding elements.

According to the invention it is suggested that specifically the holding elements for the containers or preforms are sterilised. These holding elements may be such holding elements which come into contact with the containers in order to transport them, such as for example gripping clamps and in particular also mandrels which engage in the mouth of the containers. Preferably, at least those areas of the holding elements are sterilised which subsequently come into contact with the containers or preforms.

The cleaning device is advantageously stationary and is particularly preferably disposed in an area of the transport path of the containers.

In a further advantageous embodiment, the apparatus includes a take-over zone in which it takes the containers over, and a transfer zone in which it passes the containers on. For example, it is possible for the transport device to be implemented as a transport chain which takes the containers from a transfer wheel and passes them on to a further star wheel or to a blow moulding machine.

In a further advantageous embodiment, the cleaning device is disposed in a zone of the transport path, in which during working operation of the apparatus no containers are present. Advantageously, therefore, the cleaning device is disposed in the transport direction of the holding elements between the transfer zone and the take-over zone and in this zone, no containers are carried. In this way, a particularly efficient sterilisation of the holding elements themselves is made possible.

The transport path, along which the holding elements are guided, is preferably a closed path as may be achieved, for example, if the transport device is a continuous transport chain or a star wheel.

In a further advantageous embodiment, the apparatus includes at least one heating element, in order to heat the containers along the transport path. As mentioned above, in the blow forming processes known from the prior art, the preforms are initially heated up and then expanded into plastic containers in a heated condition. To this end, continuous ovens are known from the prior art, within which the plastic preforms are heated. In this preferred embodiment it is suggested to dispose the cleaning device in an area of such an oven. This offers the advantage that, due to the heating process, also the holding elements will be at a temperature which is above room temperature, and due to this elevated temperature, also a sterilisation of the holding elements in an improved manner is made possible. However, it would also be possible to dispose the cleaning device on other transport devices such as for example transfer star wheels or the like.

The heating elements may for example be infrared heaters or the like. However, also the use of microwave heaters would be conceivable.

In a further advantageous embodiment, the cleaning device includes a container having a sterilisation liquid associated therewith. This sterilisation liquid may for example be hydrogen peroxide ($H_2O_2$), alcohol, an alkaline solution, foam, peracetic acid or hot water or similar liquids having a sterilising effect. The heating elements, for example the mandrels or heating mandrels on which the containers are placed, are at least briefly immersed into this liquid. In a further advantageous embodiment, the holding elements may be immersed into the sterilisation liquid.

Here, particularly preferably, the holding elements may, in particular in the area of the cleaning device, be moved vertically relative to the transport device, with it being sufficient for at least one vertical component to be present and for instance the holding elements to be moved at an angle. It would however also be possible to provide nozzles in the area of the cleaning device for wetting the holding elements with a sterile medium. Also other cleaning devices such as for example electron beam emitters or UV radiators may be provided in the area of the cleaning device. Also, several different cleaning devices such as nozzles or dip tanks may be provided.

The apparatus according to the invention allows a sterile processing of plastic preforms, in particular in a heating module and in particular during operation, to be carried out. In this way, permanent sterility of the preform receptacle in the heating module may be ensured. Preferably, cleaning is carried out shortly after the plastic preform has been passed on to a further device such as a blow moulding machine and shortly before a new plastic preform is fetched from an oven inlet. Preferably, the holding elements include holding mandrels which engage in the mouth of the containers. Preferably, these holding elements are placed on a transport chain or, as was mentioned above, on a transport star wheel. Sterilisation, however, may also be provided by devices other than said oven.

In a further advantageous embodiment, the cleaning device includes at least one brush device for cleaning the holding elements. This may for example be a rotatable brush device, on the opposite side of which the holding element rolls off. It would also be conceivable to provide two brush devices arranged opposite one another, between which the holding element is passed. It would also be possible to feed one or more brush elements to the holding elements.

In a further advantageous embodiment, a drying device for drying the holding elements is provided in the transport direction of the holding elements downstream of the cleaning device. Preferably, this drying device is disposed in an area in which no new containers have been received yet. It would thus be possible for the holding element or the preform receptacle to be immersed into a container containing a sterile medium, to pass through said container for several seconds and then to be dried with sterile air or gas after it has re-emerged. In this way it is prevented that any residues from the liquid get into the plastic preform.

It would further also be possible, as mentioned above, to spray a sterile medium onto the holding element, advantageously during continuous rotation of the holding element, in order to allow a uniform distribution. Subsequently, the preform receptacle or the holding element may again be dried with sterile air or with a gas, in order to remove any residues.

Preferably, the above-mentioned mandrels for receiving the plastic preforms are therefore arranged to rotate. This rotational arrangement is known per se from the prior art, in order to enable the plastic preforms to be heated along their entire circumference. However, the rotation is continued here also in the area of the sterilisation device and in particular in the area of the drying device.

It would further also be possible to dry the heating mandrels directly by means of the heating section of the apparatus. Thus, an empty run may be provided, in which the heating mandrels run through the heating section in order to be dried, whilst for example infrared lamps of the heating device remain switched on.

By means of this approach also shielding plates may be kept sterile, which particularly protect the threads of the plastic preforms.

The present invention is further directed to a system for treating containers, which comprises an apparatus of the above-mentioned kind and a moulding unit for moulding the plastic preforms into plastic bottles. Advantageously, the moulding unit is arranged here in the transport direction of the containers downstream of the above-mentioned apparatus.

In a further advantageous embodiment, the system includes further cleaning units which sterilise the containers themselves, and in particular such cleaning units which sterilise an internal wall of said containers.

The present invention is further directed to a method for treating containers, wherein the containers are transported in a transport device along a specified transport path, wherein the containers are transported in an isolated manner by means of a plurality of holding elements arranged on a transport device.

According to the invention, the holding elements are sterilised along a section of the transport path at least in sections.

Advantageously, the holding elements are sterilised in a section in which they have no containers present thereon.

In a further advantageous method, the containers are taken over from the transport device in a take-over zone and are passed on by the transport device in a transfer zone.

In a further advantageous embodiment, the holding elements are dried upon sterilisation. It is possible here for the holding elements to be first lowered into a dip tank or to be sprayed and subsequently dried.

Advantageously, the containers are heated along their transport path.

BRIEF DESCRIPTION OF THE DRAWINGS

Further advantages and embodiments will become evident from the attached drawings, wherein:

FIGS. 16a,b show two views of a further embodiment of the present invention;

FIGS. 17a,b show two views of a further embodiment of the present invention; and FIG. 18 shows a further view for illustrating the embodiments shown in FIGS. 17ab.

DETAILED DESCRIPTION OF THE INVENTION

Figure 1:
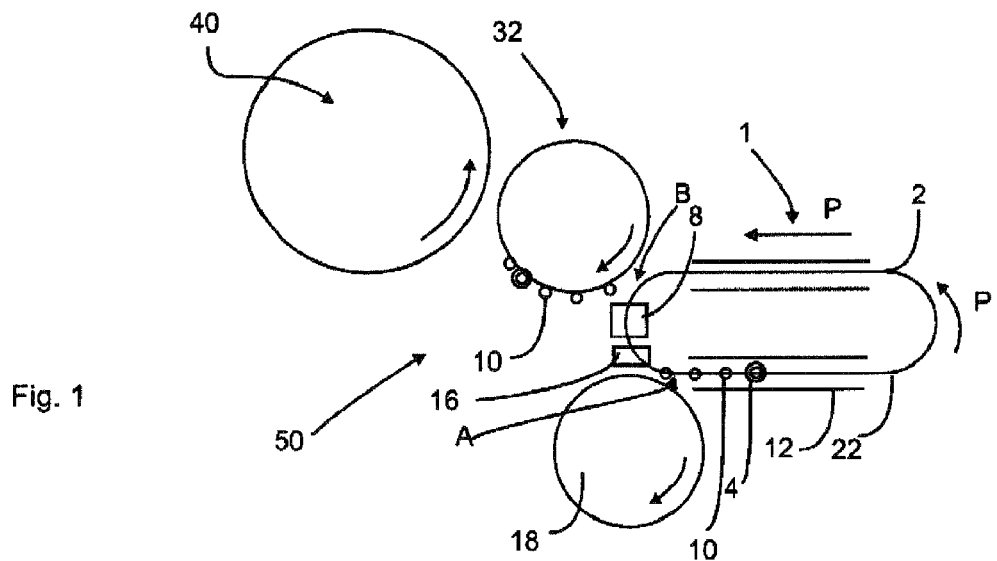
FIG. 1 shows a schematic view of a system according to the invention.

FIG. 1 shows a system according to the invention for manufacturing plastic containers. This system includes an apparatus 1 such as heating means which heat plastic preforms 10. Here, the plastic preforms are transported by means of a transport device 2 along a transport path P and are heated in this zone by heating elements 12. The containers which are subsequently warm are passed on to a transfer star wheel 32 and from there to a moulding unit 40. This moulding unit 40 includes a plurality of blow moulding stations (not shown), which expand the plastic preforms into plastic containers.

Reference numeral 4 identifies a holding element which is only schematically shown, which holds or carries respectively one plastic preform 10 so that it can be transported. The plastic preforms 10 are passed on to the apparatus 1 by a transfer star wheel 18.

Reference letter A refers to a take-over zone in which the plastic preforms are passed on to the apparatus 1 by the transport star wheel 18. Reference letter B identifies a transfer zone in which the plastic preforms are passed on to the transport star wheel 32 by the transport device 2. Between this transfer zone B and the take-over zone A, a cleaning device 8 which sterilises the holding elements is provided in the transport direction of the holding elements 4, which is here the counter-clockwise direction. Downstream of this cleaning device 8, a drying device 16 is provided which dries the sterilised holding elements 4.

Figure 2:
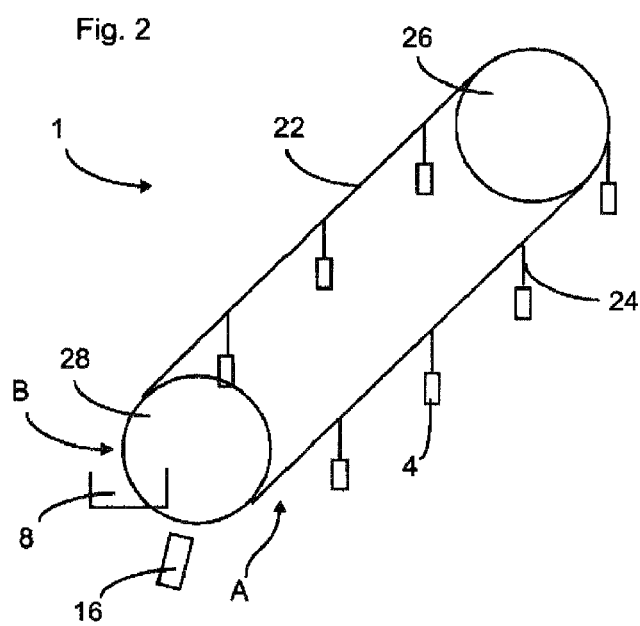
FIG. 2 shows a schematic view of an apparatus according to the invention.

FIG. 2 shows an apparatus 1 according to the invention. In this embodiment, the transport device 2 has a transport chain 22 circulating about two diversion wheels 26, 28, which transport chain has a plurality of holding elements 4 provided thereon. These holding elements 4 are implemented here as mandrels or heating mandrels which protrude into the containers and which in turn are fastened to carrier rods 24 which are mounted on the transport chain 22. Downstream of the transfer zone, i.e. once the holding elements 4 have passed on the containers (not shown), they are guided through a cleaning device 8, which is arranged here to be stationary and in which a cleaning medium, in particular a liquid such as nitrogen peroxide, is provided. The cleaning device 8 is followed by the drying device 16.

Figure 3:
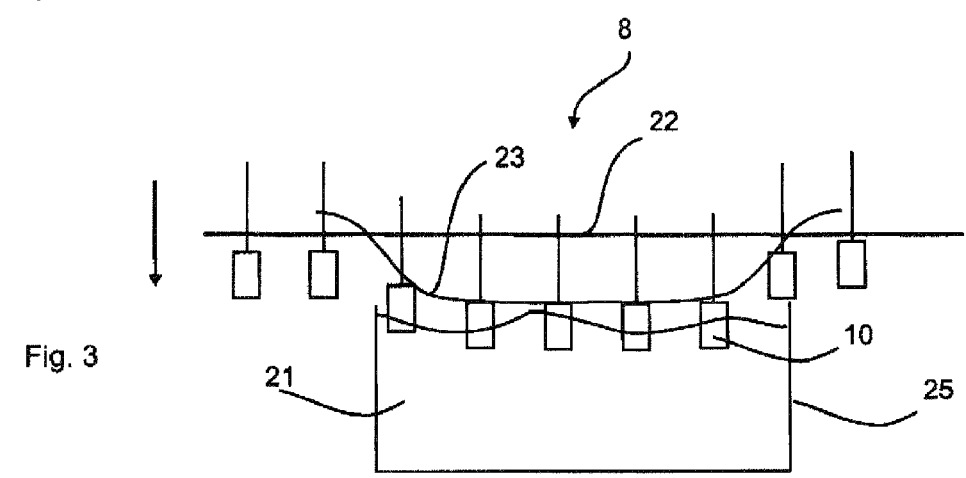
FIG. 3 shows a detailed view of the apparatus from FIG. 2.

FIG. 3 shows a possible embodiment of a cleaning device 8 according to the invention. Here, the cleaning device 8 includes a container 25 into which the individual holding elements 4 are immersed. To this end, a guide curve is provided which pushes the holding elements 4 downwards along the arrow y in the area of the container 25 and thus immerses them into the liquid 21. By this means, the guide curve ensures that the holding elements will come back up after having been immersed. To this end, spring means may be provided on the holding elements 4 or the carrier rods 24 thereof, which spring means push the holding elements 4 back up. In addition or instead of this, as mentioned above, cleaning nozzles may be provided which spray a sterilisation medium onto the individual holding elements 4.

Figure 4:
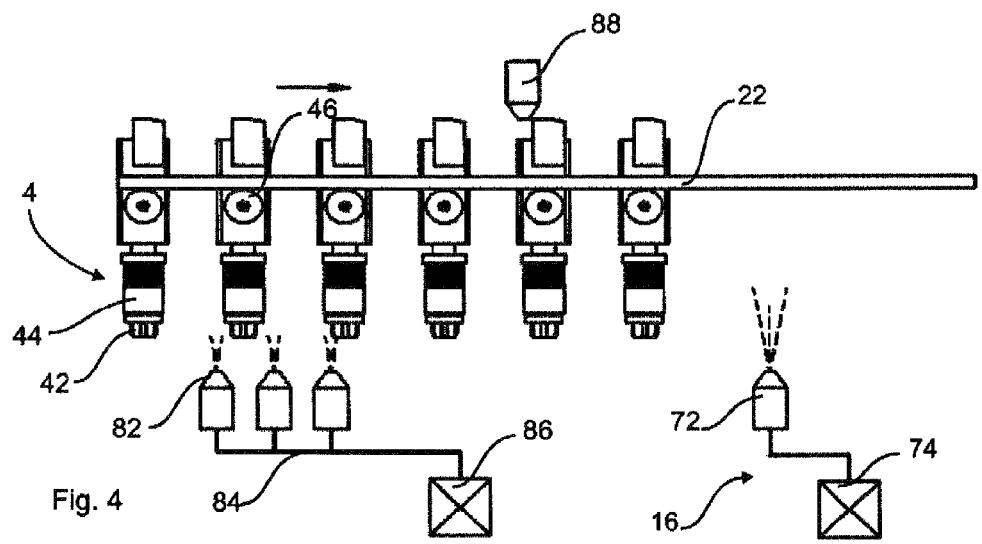
FIG. 4 shows a detailed view of an apparatus according to the invention.

FIG. 4 shows a further detailed view of an apparatus according to the invention. In this embodiment, the individual holding elements 4 are conveyed in a horizontal direction. The holding elements here include a mandrel 42 which engages in a mouth of the container (not shown) and which is disposed on a carrier 44. In this embodiment, the holding elements 4 are sprayed using a plurality of nozzles 82 and are sterilised in this way. Additionally, a further nozzle 88 for internal sterilisation is provided. Reference numeral 84 relates to a supply line for feeding a sterilisation medium to the individual nozzles 82, and reference numeral 86 refers to a reservoir for the liquid. Thus, the individual heating mandrels 42 are sprayed here with a sterile medium, wherein advantageously the heating mandrels are first driven into rotation or are rotated during the spraying process. Subsequently, the heating mandrels 42 are dried using a sterile air blower 72 which is also connected to a reservoir 74 and which as a whole constitutes a drying device 16.

Figure 5:
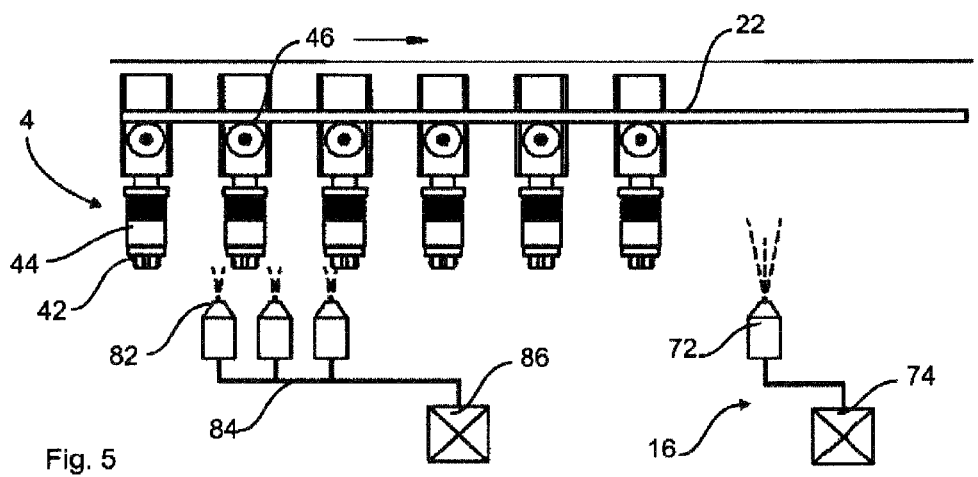
FIG. 5 shows a further detailed view of an apparatus according to the invention.

In the embodiment shown in FIG. 5, the nozzle 88 for internally cleaning the holding elements 4 was omitted. Reference numeral 46 relates to a cam roller which is disposed on the holding elements 4 and which is used for guiding in relation to a cam 22.

Figure 6:
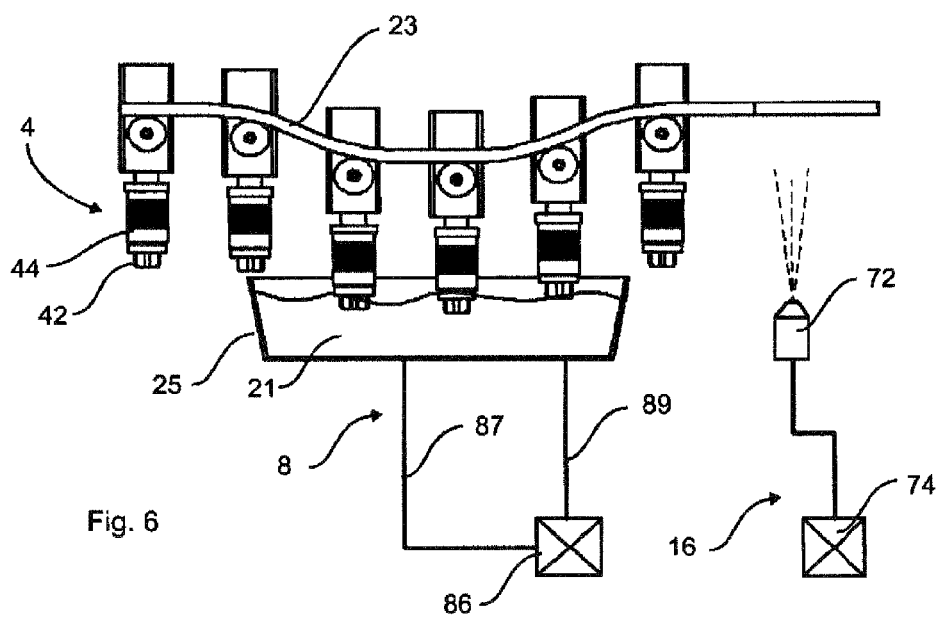
FIG. 6 shows a view of a further embodiment of an apparatus according to the invention.

FIG. 6 shows a more detailed view of an apparatus according to the invention. Here, as was already shown in FIG. 3, the holding elements 4 are pushed downwards by a specific guide curve 23 and the mandrels 42 are immersed into a sterile liquid 21. Reference numeral 86 again identifies a reservoir for the sterile liquid, however, a feed 89 from the reservoir into the container 25 as well as a return feed 87 are provided here. In this embodiment, too, a drying device 16 of the above-mentioned kind is provided downstream with regard to the cleaning device 8.

Figure 7:
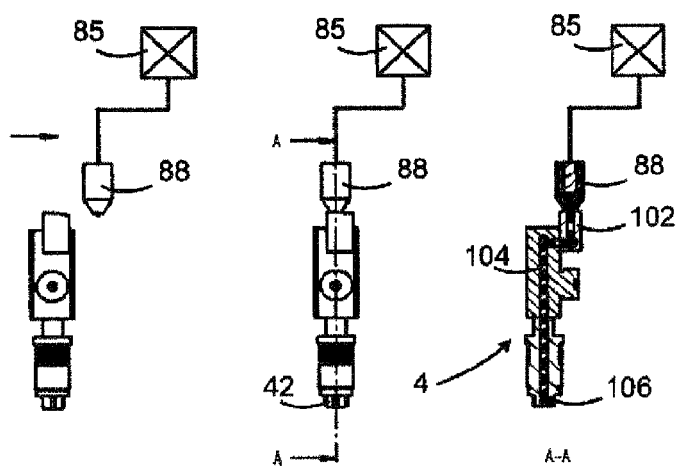
FIG. 7 shows three sectional views for illustrating an internal sterilisation.

FIG. 7 shows a simplified view for illustrating the internal sterilisation process. The nozzles 88 are here additionally equipped with a valve (not shown), which opens when passing the heating mandrels. When this valve opens, sterile liquid may flow via a channel on the inside of the heating mandrel for example up to the clamping jaws and can thus sterilise the locations that will later come into contact with the preform.

On the left hand side, FIG. 7 shows a situation prior to a contact, with the valve that feeds the sterile liquid being closed. According to the view in the middle, the nozzle 88 comes into contact with a bearing block 102, which is here laterally provided on the holding element 4 and causes the valve (not shown) to open. In this way, a sterile medium is released and flows through the holding element. On the right hand side, FIG. 7 shows a section along the lines A-A according to the view in the middle. What is shown here on the inside of the holding element 4 is a channel 104 for transporting the sterile medium in the direction of the mandrel 42. Further, radially extending channels 106 are provided (not shown in detail), which convey the sterile liquid to the outside of the heating mandrel 42.

Figure 8:
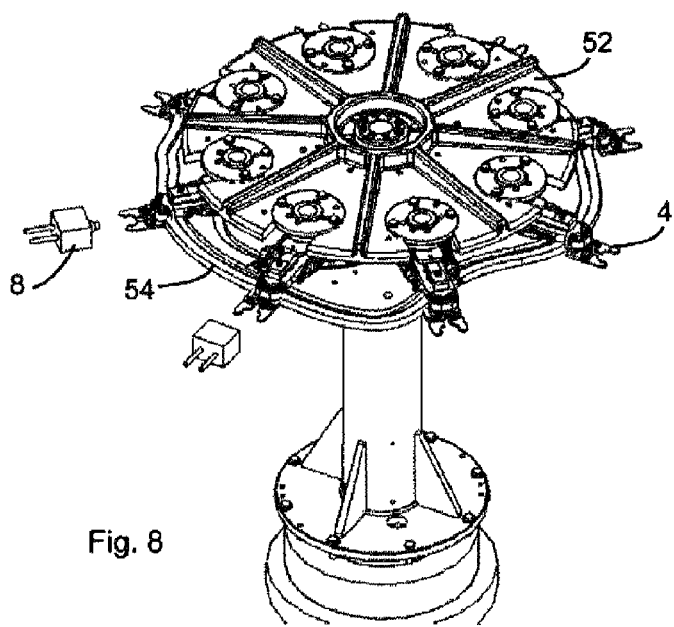
FIG. 8 shows a view of a further embodiment of an apparatus according to the invention.

FIGS. 8-12 show a further embodiment of an apparatus according to the invention, and in this case the holding elements 4 are gripping clamps which grip the container around its external circumference, for instance below the bearer ring. Reference numeral 52 identifies a carrier wheel on which a plurality of holding elements 4 are arranged. Here, too, cleaning devices 8 are provided radially outside of these holding elements, which will apply here a sterile medium onto the holding elements 4 in a radial direction. As shown in FIG. 8, several cleaning devices may be disposed here around the outer circumference. Preferably, the cleaning device 8 is disposed to be stationary here as well.

Figure 9:
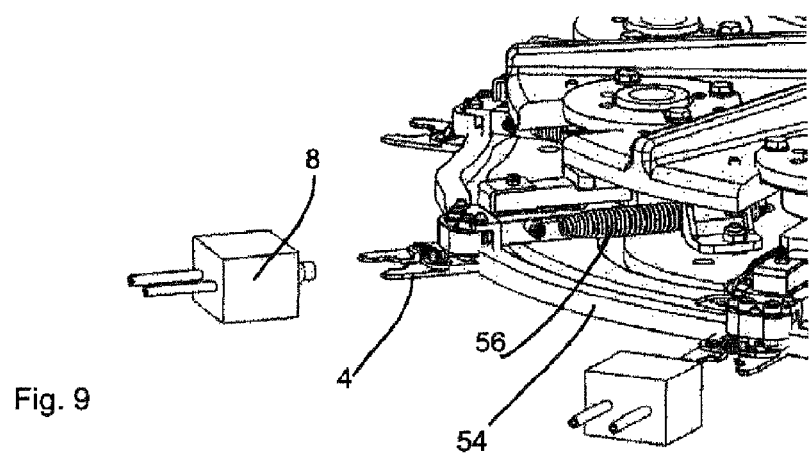
FIG. 9 shows a detailed view of the apparatus of FIG. 8.

FIG. 9 shows a detailed view of the apparatus shown in FIG. 8. It can be seen here that the apparatus also has a guide curve 54 which pushes the holding elements radially outwards when these pass the cleaning devices 8 in the circumferential direction. A spring element 56 causes the holding elements to be pulled back again in a radial direction, so that they will follow the path of the guide curve 54.

Figure 10:
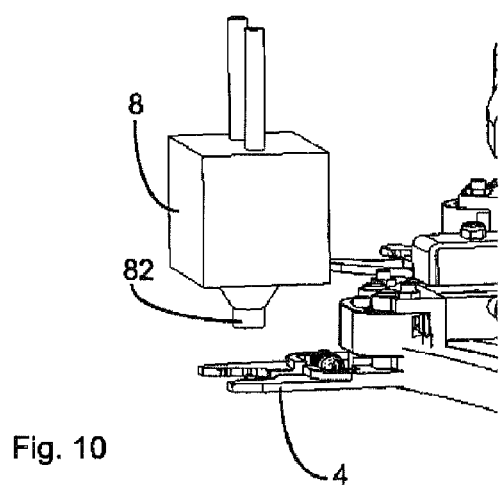
FIG. 10 shows a further embodiment of an apparatus according to the invention.

FIG. 10 shows a further embodiment of a cleaning device according to the invention, however, sterilisation is carried out here from the top. The triggering or actuation of a valve (not shown) of this cleaning device 8 could for example be carried out independence of a rotary position of the holding elements 4, but other control mechanisms would also be possible, such as for example a light barrier control.

Figure 11:
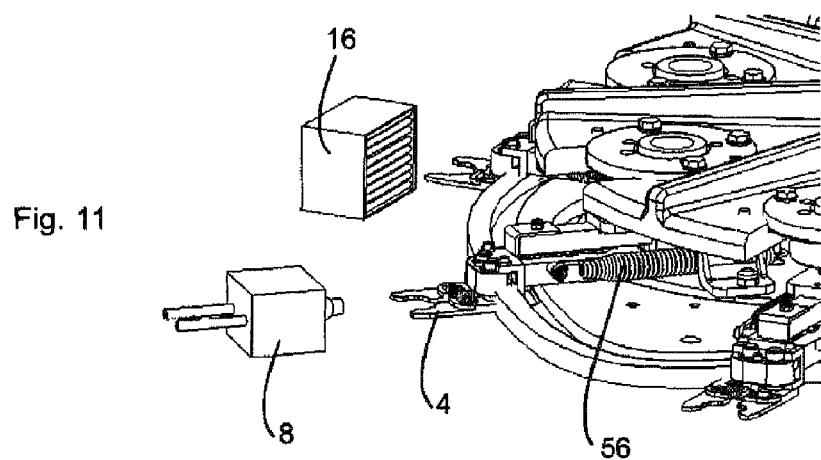
FIG. 11 shows a further embodiment of an apparatus according to the invention.

FIG. 11 shows a further embodiment of an apparatus according to the invention, and here a drying device 16 is shown downstream relative to the cleaning device, which for example applies air to the holding elements 4.

Figure 12:
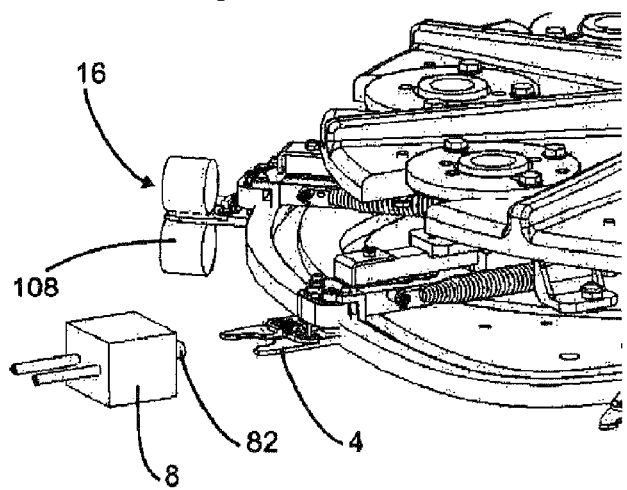
FIG. 12 shows a further embodiment of an apparatus according to the invention.

FIG. 12 shows a further embodiment of an apparatus according to the invention. Instead of a drying device implemented as a ventilation device, the drying device here has two rollers 108, between which the holding elements 4 are passed and which are used for drying the holding elements 4.

These rollers 108, however, could also be implemented as brushes for cleaning the holding elements, or a further roller pair (not shown) could be provided. Such brushes could particularly be designed in such a way that the internal areas of the holding elements 4 are cleaned as well.

It is noted that said rollers may be used not just for drying but, if required, also for sterilisation, if a suitable sterilisation medium is applied.

Thus, by means of the process according to the invention, the most varied holding elements may be sterilised. As is the case with the heating mandrels, also in the case of the gripping clamps sterilisation liquid may be applied using the nozzles, and if required, these may be dried again with sterile air using a second nozzle. As mentioned, infrared radiation may be suitable for drying, but also for activating the sterilisation liquid. It is conceivable to carry out the drying process shown here, as well as the sterilisation, however, from different sides or, if needed, also from the bottom. Apart from that, it would also be possible to clean the holding elements 4 using brushes. It would be possible here, as mentioned, for the brushes or rollers to apply additionally sterilisation liquid, by providing them with a through-passage on the inside.

Apart from that, also a drip protection (not shown) may be provided here, which ensures that the liquid, i.e. the sterilisation medium, is not distributed over the entire machine. This dripping protection could also recycle the sterilisation medium back to a processing unit.

Apart from that, sensors, in particular optical sensors which check the holding elements in periodic intervals for contamination or sterility, could further be provided. Cleaning of the holding elements may be carried out either in a cleaning cycle, in which the machine may be operated at a lower speed, or continuously during working operation. In particular in the latter case it would be preferred, as mentioned above, to carry out sterilisation or cleaning in an area in which no preform is in engagement, i.e. in the case of heating mandrels, after the transfer of the preform to the transport star wheel and prior to a new take-over of a plastic preform. In the case of clamps, this could be the area downstream of the location where the plastic preform is passed on to the blow wheel and prior to a new reception of the plastic preform by the heating module.

Figure 13:
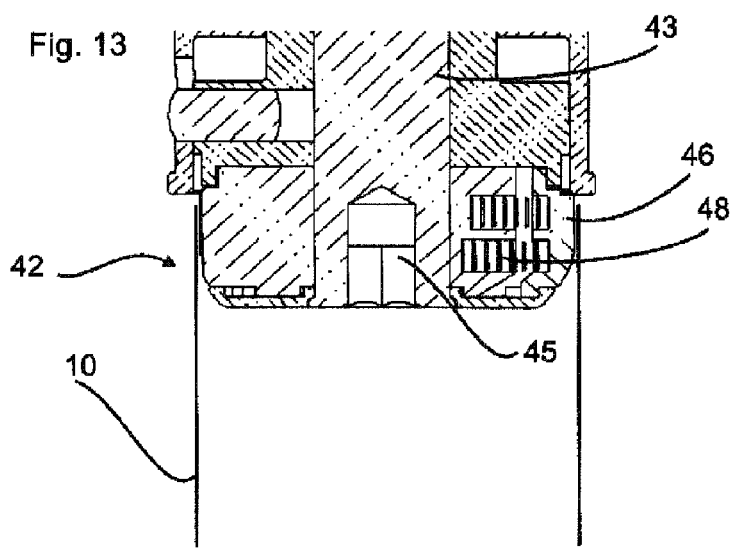
FIG. 13 shows a view of a holding element.

FIG. 13 shows a view of a heating mandrel 42 on which a plastic preform 10 (which is shown only partially and is only indicated) is held. Reception elements 46 are provided on this heating mandrel, which are spring-loaded by spring elements 48 or are pushed radially outwards. Further, connection means such as a screw 45 are provided to enable the holding mandrel 42 to be taken off from a bar 43. The spring means 48 is here preferably made from a material such as V4A (stainless steel) in order to be able to resist corrosion and to withstand in particular the application of sterilisation media.

Figure 14:
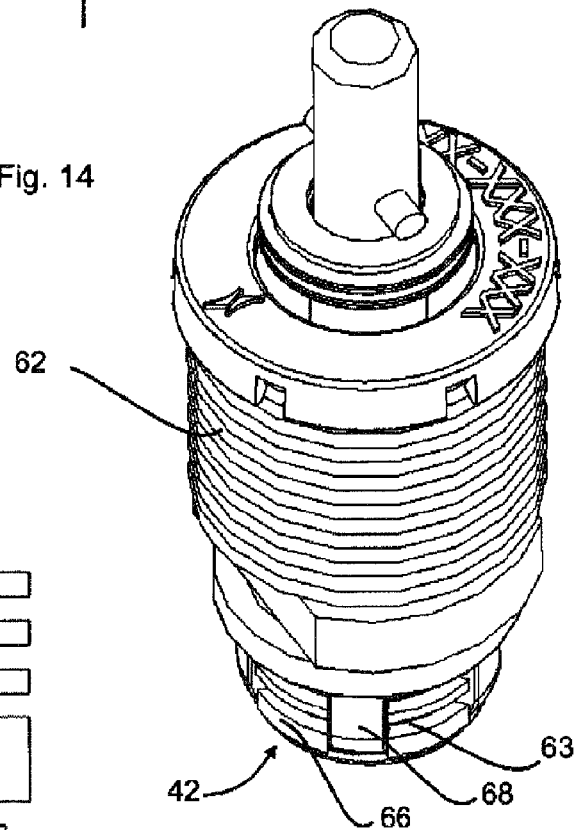
FIG. 14 shows a view of a holding element in a further embodiment.

FIG. 14 shows a further embodiment of a holding element according to the invention. In this case, a heating mandrel 42 having O-rings is provided, which O-rings are advantageously disposed in grooves 63.

Figure 15:
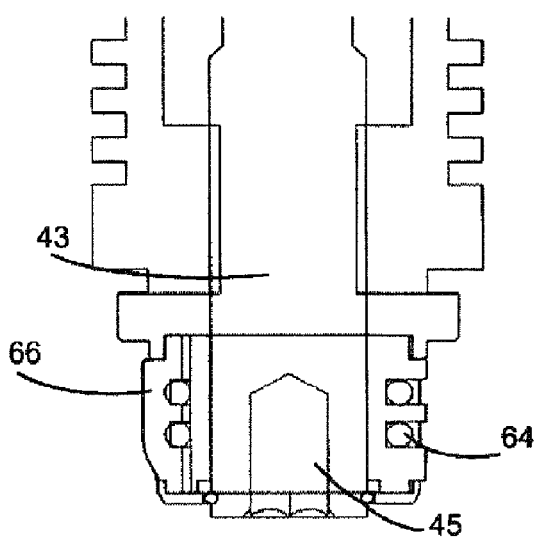
FIG. 15 shows a sectional view of the holding element shown in FIG. 14.

FIG. 15 shows a corresponding sectional view of the heating mandrel shown in FIG. 14. What can be seen here are, in particular, the individual O-rings 64 which are advantageously made from materials such as EPDM (ethylene propylene diene) rubber, perfluorine rubber such as e.g. FFKM or a suitable composite material. Apart from that it would also be possible to use Teflon rings as O-rings 64. These O-rings are disposed here in the grooves 63 shown in FIG. 14 and push the reception elements 66 radially outwards. This means that the O-rings 64 exert a spring action on the reception elements 66. However, these reception elements 66 are not arranged all the way round the circumference, but recesses 68 are provided between two fastening means 66, as shown in FIG. 14. In this case, too, the holding mandrel is disposed on a rod 43 by means of a connection device 45. The above-explained steps for internal sterilisation, however, are not shown here.

FIGS. 16a and 16b show a further embodiment of the present invention. In addition to the embodiment shown in FIG. 7, a cover means 90 such as a so-called CIP cap is provided here, which is disposed below the holding element 4. In this embodiment, this cover means is pivotably disposed opposite the holding element 4. Thus, it is possible for these cover means to be pivotably supported in such a way that they move along with an oven chain (not shown). It would also be conceivable for the CIP caps 90 not to be associated with each holding element, but to be disposed to be stationary, in order to enable a cyclical cleaning regime of the holding elements 4. It would also be conceivable to have the CIP caps 90 accompany the holding elements 4 for certain periods of time. In this way, a continuous cleaning process along the accompanying section would be possible.

Advantageously, therefore, a cover means 90 is provided on at least one holding element 4, and a cleaning liquid may be guided across this cover means 90 at least in sections.

Reference numeral 112 in FIG. 16b correspondingly identifies a guide curve arranged to be stationary, by means of which a roller 92 provided on the cover means 90 may be moved in order to pivot the cover means (in the figure plane according to FIG. 16b). This guide curve is here additionally pivotable or extendable by means of driving means such as a pneumatic cylinder 114. It is possible here for a second curve segment 112c to be displaceable relative to a first curve segment 112a, in order to adjust the guide curve 112. Reference numeral 112b refers to a corresponding transition segment. By means of the adaptation of the curve 112 as schematically shown in FIG. 16b of a pivoting process of the cover means may be achieved. However, in the same way it would also be possible to feed or displace the curve segments 112a, 112b and 112c together.

Reference numeral 94 in FIG. 16a identifies an articulation such as a pivot shaft, about which the cover means 90 may be pivoted. Reference numeral 98 identifies sealing means for sealing the holding element (in particular during a rinsing process).

For cleaning purposes, a cleaning or sterilisation medium passes here (preferably continuously), via a rotary distributor in the oven, through the heating mandrel and/or the shielding plate and is recycled by the CIP cap via a return line (not shown). Also conceivable would be servo feeds for the caps.

The heating mandrels are preferably sterilised in this way on a continuous oven (for example STIR (selective transformed infrared) or a microwave oven). In this way, a simpler rotary distribution would be achieved. It would also be conceivable to clean/sterilise in this way the heating cavities associated with one or several preforms, i.e. for example the resonators or heating pockets.

FIGS. 17a and 17b show a further embodiment of the present invention. Here, so-called heating receptacles 120 or heating pockets are provided, in which the plastic preforms are heated during working operation. These heating receptacles move together with the plastic preforms. Thus, these heating receptacles 120 act as radiation chambers surrounding the preforms. These heating receptacles may be arranged in the form of a carousel. Reference numeral 122 refers to infrared radiators which heat the plastic preforms arranged in the reception space 124.

An internal wall of the heating receptacles 120 may here be formed as a ceramic infrared radiator. Apart from that it would be possible to insert a rod-shaped infrared radiator (not shown) into the plastic preforms, in order to heat the latter. Advantageously, the plastic preform is here completely positioned (if necessary with the exception of its mouth) inside the heating receptacle. However, the heating element 4 or the heating mandrel itself does not need to be formed as an IR radiator, but could for instance just reflect or hold the plastic preform. Reference numeral 126 identifies a protective plate for the IR radiator.

FIG. 17b shows the heating receptacle 120 in a cleaning operation. Here, this heating receptacle is sterilised by filling it with the sterilisation medium 130. More specifically, here also the heating radiators 122 and the reflectors could be cleaned. Reference numeral 132 refers to a bottom of the heating receptacle, which here also forms an outlet for the sterilisation medium 130. For opening, the bottom could be pivoted about a pivot axis 134. FIG. 17a additionally shows a return channel 118 serving for returning the sterilisation medium. The heating receptacle 120 may in particular be filled by the holding element 4 itself. Thus, it is not urgently necessary for the mandrel 4 to have its own cover means 90. In this way, it is also possible to immerse the holding element 4 for cleaning or sterilising the external surfaces. In other words, the heating receptacle 120 could take over in this way the function of the cover means 90.

FIG. 18 shows a further view for illustrating a sterilisation process. The cleaning medium is fed via the channel 104 into a reception space 140 formed by the cover means 90. From there, the cleaning medium flows back up (arrow P2) via the return channel 118. To this end, the cover means 90 is pressed against a stop 152, which stop may serve also as a stop for the plastic preforms during working operation of the system.

Reference numeral 142 refers to a gripper jaw used for holding the plastic preforms. These gripper jaws 142 may be cleaned as well. To this end, the holding element includes a partial channel 154 which is used for rinsing behind the gripper jaws 142. Reference numeral 98 again refers to sealing means for sealing the cover means 90 against the holding element during the rinsing operation. By means of a spring means 146 (which, however, may also be an elastic O-ring), the gripping jaw 142 is biased outwards. Reference numeral 144 identifies a holding space for holding the gripping jaw 142. In other words, the holding element 4 is cleaned or sterilised both on the inside and on the outside.

The cover elements 90 shown in FIGS. 16 to 18 may also be formed at least partially from a reflective material for reflecting radiation during normal operation of the apparatus, in particular onto the preform.

Cleaning or sterilisation liquid may also be used for cooling individual elements such as heating mandrels during normal operation.

Apart from that it is noted that the present invention can also be used for such machines which heat the plastic preforms in their circumferential direction in an irregular manner (preferential heating). An apparatus of this kind is illustrated for example in the so far unpublished German Patent Application No. 10 2009 021 792.4. The contents of this application are herewith included in their entirety in the contents of the present application by reference.

Here, for example, clamps may be cleaned which contact the plastic preforms, in order to apply thereto in this way an irregular temperature profile. Cleaning could also be carried out here by means of brushes or also in a CIP mode.

Apart from that, it would also be possible to carry out cleaning of a sterilisation module as described in PCT/EP2009/059923. The contents of this application are herewith included in their entirety in the contents of the present application by reference as well.

The Applicant reserves the right to claim all of the features disclosed in the application document as essential to the invention, in as far as they are novel over the prior art either individually or in combination.

LIST OF REFERENCE NUMERALS

1 Apparatus
2 Transport device
4 Holding elements
8 Cleaning device
10 Containers
12 Heating element
14 Container
16 Drying device
18 Transfer star wheel
21 Sterile medium
22 Transport chain
23 Guide curve
24 Carrier rod
25 Container
26, 28 Diversion wheel
32 Transfer star wheel, transport star wheel
40 Moulding unit
42 Mandrel, heating mandrel
43 Rod
44 Carrier
45 Screw
46 Reception element
48 Spring element
50 System
52 Carrier wheel
54 Guide curve
56 Spring element
63 Groove
64 O-ring
66 Reception element
68 Recess
72 Sterile air blower
74 Reservoir
82 Nozzle
84 Supply line
86 Reservoir
87 Return feed
88 Nozzle
89 Feed
90 Cover means
92 Roller
94 Articulation
98 Sealing means
102 Bearing block
104 Channel
106 Channels
108 Roller
112 Guide curve
112a-c Segments of the guide curve
114 Pneumatic cylinder
118 Return channel
120 Heating receptacle
122 Infrared radiator
124 Reception space
126 Protection plate
130 Sterilisation medium
132 Bottom of the heating receptacle 120

134 Pivot axis
140 Reception space
142 Gripper jaw
144 Holding space
146 Spring means
152 Stop
154 Partial channel
A Take-over zone
B Transfer zone
P Transport path
P1, P2 Arrows

The invention claimed is:

1. An apparatus for moulding plastic preforms into plastic containers, including a transport device which transports the containers along a specified transport path (P), the transport device having a plurality of holding elements for holding the containers, with the holding elements being continuously transported along the specified transport path (P),
wherein the holding elements include at least a rotatable mandrel which engages in a mouth of the plastic preforms and which is disposed on a carrier, wherein reception elements are provided on this rotatable mandrel, which are one of spring-loaded by spring elements or pushed radially outwards,
wherein the apparatus further includes a cleaning device for cleaning the holding elements at least in sections and has at least one preform heating element for heating the plastic preforms along the transport path (P)
the apparatus further comprising a moulding unit which includes a plurality of blow moulding stations, which expand the plastic preforms into plastic containers,
wherein a sterilizer for internal sterilization of the mandrel is provided which is connected to a reservoir for a sterilization agent, the mandrel passing the stationary reservoir during transportation.

2. The apparatus as claimed in claim 1, wherein the apparatus includes a take-over zone (A) in which it takes over the containers, and a transfer zone (B) in which it passes the containers on.

3. The apparatus as claimed in claim 1, wherein the cleaning device is disposed in a zone (C) of the transport path (P), in which no containers are present during working operation of the apparatus.

4. The apparatus as claimed in claim 1, wherein the cleaning device includes a container having a sterilization liquid provided therein.

5. The apparatus as claimed in claim 4, wherein the containers may be immersed into the liquid.

6. The apparatus as claimed in claim 1, wherein the holding elements include holding mandrels which engage in the mouth of the containers.

7. The apparatus as claimed in claim 1, wherein the cleaning device includes at least one brush for cleaning the holding elements.

8. The apparatus as claimed in claim 1, wherein a drying device for drying the holding elements is provided in the transport direction of the holding elements downstream of the cleaning device.

9. The apparatus as claimed in claim 1, wherein a cover is disposed on at least one holding element and a cleaning liquid may be guided over this cover at least in sections.

10. A system for treating containers using an apparatus as claimed in claim 1 and including a moulding unit for moulding plastic preforms into plastic bottles.

11. The system as claimed in claim 10, wherein the moulding device is arranged in a transport direction of the containers downstream of the apparatus.

12. The apparatus as claimed in claim 1, wherein cleaning of the holding elements is carried out in a cleaning cycle.

13. The apparatus as claimed in claim 1, wherein the reservoir is stationary.

14. The apparatus as claimed in claim 1, wherein the sterilization agent flows via a channel on the inside of the heating mandrel.

15. An apparatus for moulding plastic preforms into plastic containers, including a transport device which transports the containers along a specified transport path (P), the transport device having a plurality of holding elements for holding the containers, while the containers are transported along the specified transport path (P),
wherein the apparatus includes at least one of a cleaning device and a sterilizing device for cleaning and/or sterilizing the holding elements at least in sections and wherein the transport device is a star wheel and wherein the holding elements are clamps, wherein the holding elements include at least a rotatable mandrel which engages in a mouth of the plastic preforms and which is disposed on a carrier, wherein reception elements are provided on this rotatable mandrel, which are one of spring-loaded by spring elements or pushed radially outwards, and the apparatus further comprising a moulding unit which includes a plurality of blow moulding stations, which expand the plastic preforms into plastic containers, wherein a sterilizer for sterilization of the clamps is provided which is connected to a reservoir for a sterilization agent, the clamps passing the stationary reservoir during transportation.

16. The apparatus as claimed in claim 15,
wherein the apparatus includes at least one of a cleaning device and a sterilizing device for cleaning and/or sterilizing the holding elements at least in those sections which come into contact with a plastic preform or a container after a treatment with a sterilizing or cleaning agent, and
wherein the holding elements are gripping clamps which grip the container around its external circumference.

17. The apparatus as claimed in claim 16, wherein the cleaning device is disposed to be stationary.

18. The apparatus as claimed in claim 16, wherein the clamps are mounted on a transfer star wheel which transports one of the preforms into a blow moulding device or containers out of the moulding device.

19. The apparatus as claimed in claim 16, wherein cleaning of the holding elements are carried out in a cleaning cycle.

20. An apparatus for moulding plastic preforms into plastic containers, including a transport device which transports the containers along a specified transport path (P), the transport device having a plurality of holding elements in the form of gripping clamps and/or mandrels for holding the containers, with the holding elements being transported along the specified transport path (P), wherein the holding elements include at least a rotatable mandrel which engages in a mouth of the plastic preforms and which is disposed on a carrier, wherein reception elements are provided on the rotatable mandrel, which are one of spring-loaded by spring elements or pushed radially outwards,
wherein the apparatus includes at least one of a cleaning device and a sterilizing device for cleaning and/or sterilizing the holding elements at least in sections, wherein the cleaning device and/or sterilizing device is disposed in a zone (C) of the transport path (P), in which no containers are present during working operation of the apparatus in order to clean and/or sterilize those areas of the holding elements which subsequently come into contact with the containers the apparatus further comprising a moulding unit which includes a plurality of blow moulding stations, which expand the plastic preforms into plastic containers, wherein a sterilizer for internal sterilization of the mandrel is provided which is connected to a reservoir for a sterilization agent, the mandrel passing the stationary reservoir during transportation.

* * * * *